(12) United States Patent
Nishimoto

(10) Patent No.: US 7,523,641 B2
(45) Date of Patent: Apr. 28, 2009

(54) METHOD TO MEASURE EXHAUST-GAS COMPONENTS

(75) Inventor: Tetsuro Nishimoto, Hiroshima-Ken (JP)

(73) Assignee: Juon Co., Ltd., Hiroshima-ken (JP)

( * ) Notice: Subject to any disclaimer, the term of this patent is extended or adjusted under 35 U.S.C. 154(b) by 103 days.

(21) Appl. No.: 11/548,616

(22) Filed: Oct. 11, 2006

(65) Prior Publication Data
US 2008/0087071 A1 Apr. 17, 2008

(51) Int. Cl.
G01N 7/00 (2006.01)
(52) U.S. Cl. .............. 73/23.2; 73/23.31; 73/28.01
(58) Field of Classification Search ............. 73/863.24, 73/23.2, 23.31–23.33, 28.01, 28.04–28.06, 73/863.22; 55/DIG. 30; 436/163; 422/90
See application file for complete search history.

(56) References Cited

U.S. PATENT DOCUMENTS

| | | | | |
|---|---|---|---|---|
| 4,747,297 A | * | 5/1988 | Okayama et al. | 73/23.33 |
| 5,106,755 A | * | 4/1992 | Tanaka | 436/137 |
| 6,134,942 A | * | 10/2000 | Pasquereau et al. | 73/23.31 |
| 6,585,661 B1 | * | 7/2003 | Hunt et al. | 600/532 |
| 6,920,802 B2 | * | 7/2005 | Newbound | 73/863.23 |
| 7,118,537 B2 | * | 10/2006 | Baddour | 600/543 |
| 2004/0127808 A1 | * | 7/2004 | Vaughan et al. | 600/532 |
| 2006/0218905 A1 | * | 10/2006 | Alexander | 60/301 |

OTHER PUBLICATIONS

J. Fischer et al. "Method For Determination of Plasticizers in Industrial Emissions" Chromatographia vol. 37, No. 1/2, Jul. 1993, pp. 47-50.*

* cited by examiner

Primary Examiner—Daniel S Larkin
(74) Attorney, Agent, or Firm—Perkins Coie LLP

(57) ABSTRACT

A method to measure exhaust-gas components are determined by exposing a surface of a part to exhaust gas, cleansing the surface exposed to the exhaust gas with a solvent, and measuring the pH of the solvent obtained in the cleansing process. Alternatively, the electric conductivity of the solvent after the exposure is measured. The acidic matter, selectively at least one of NOx or SOx in the exhaust gas can be quantified. The larger the pH value or conductivity, the higher the density of electrolytes, selectively SOx or Nox in the exhaust gas.

11 Claims, 5 Drawing Sheets

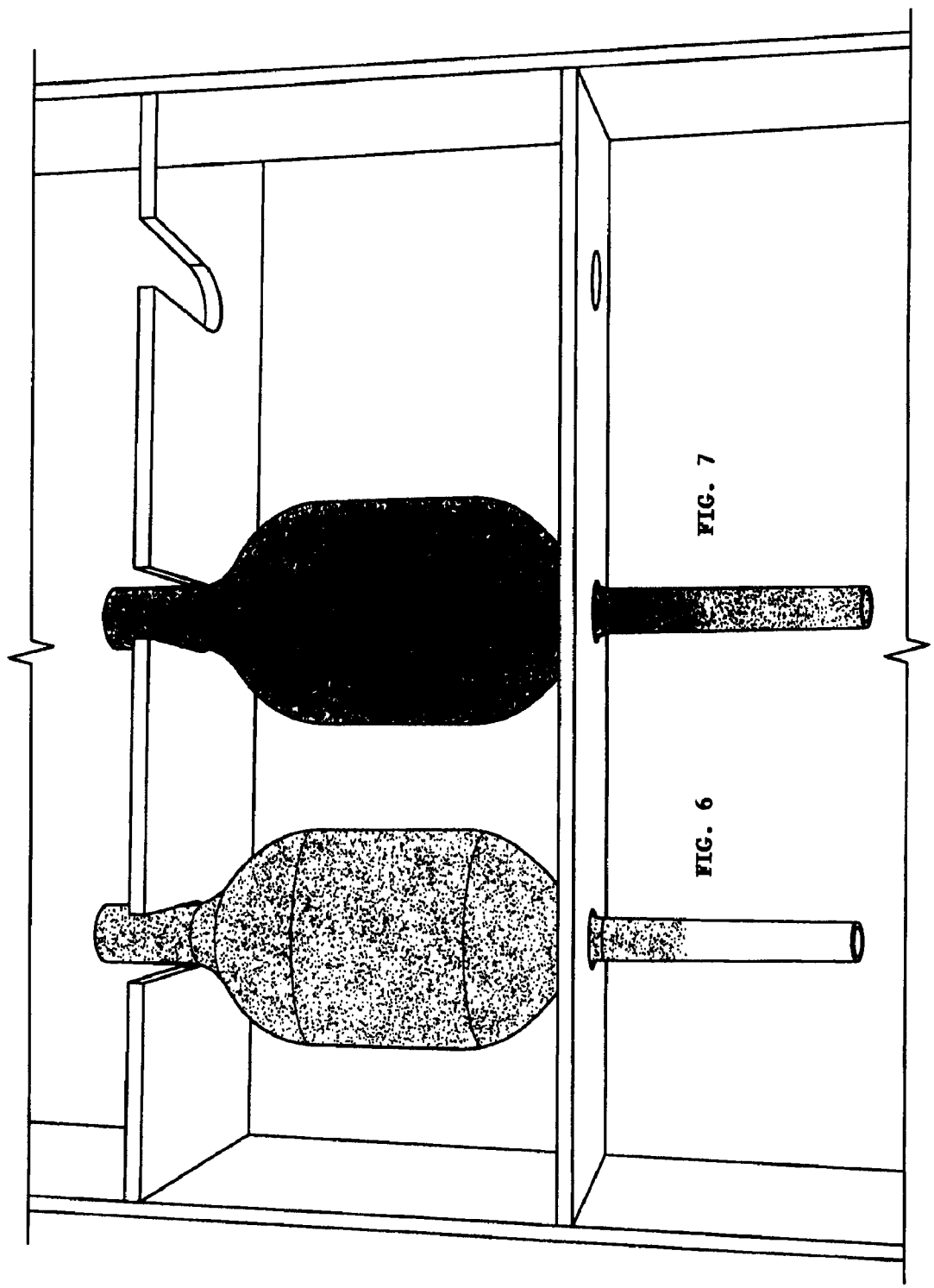

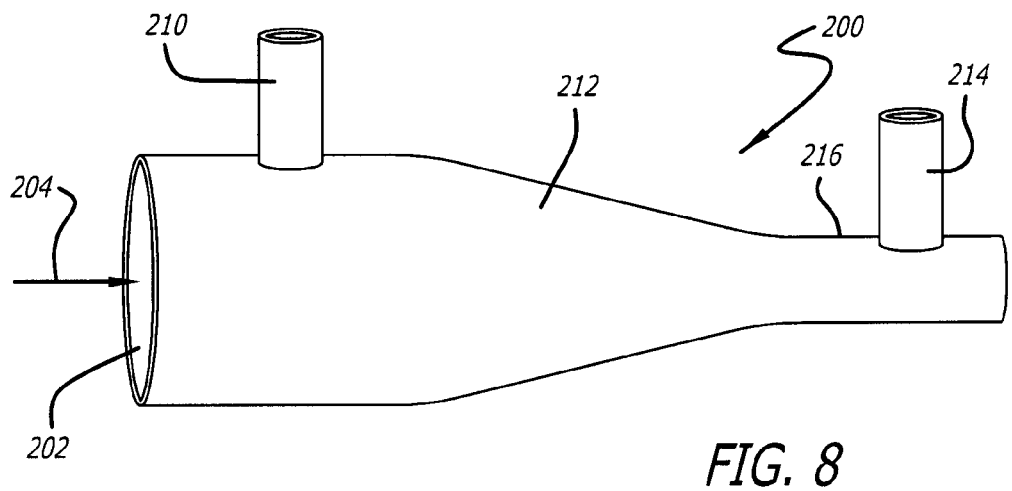
FIG. 8
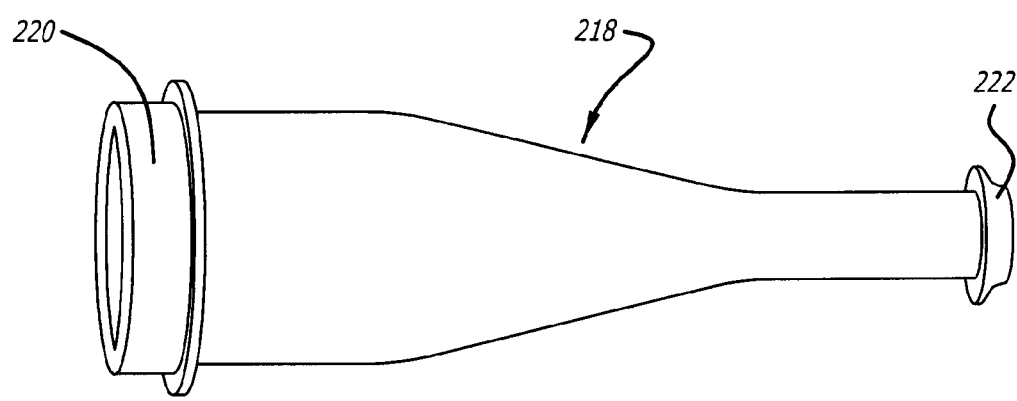
FIG. 9
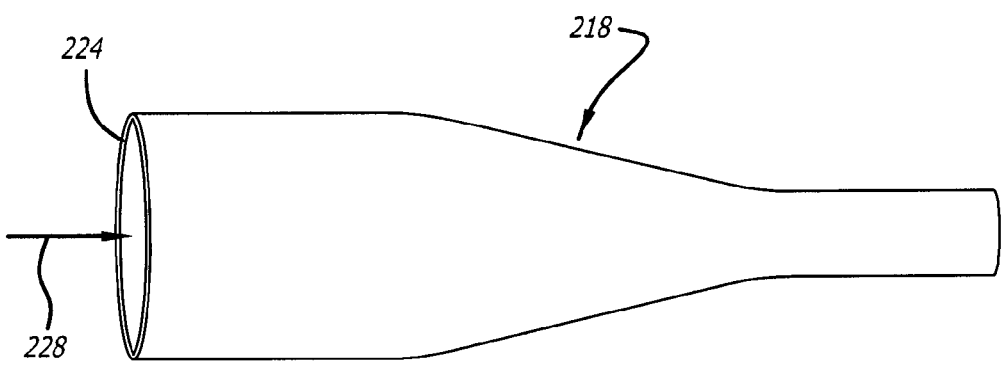
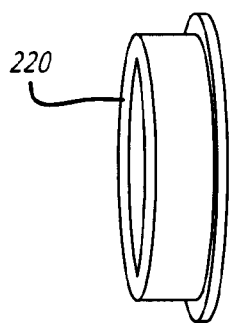
FIG. 10

US 7,523,641 B2

METHOD TO MEASURE EXHAUST-GAS COMPONENTS

BACKGROUND

This disclosure relates generally to providing an improved method of measuring exhaust-gas components conveniently and efficiently.

SUMMARY

A method of measuring exhaust-gas components comprises exposing a surface of a part to exhaust gas, cleansing the surface exposed to the exhaust-gas with a solvent, and measuring the pH of the solvent obtained in the cleansing process.

In another form a method of measuring exhaust-gas components comprises exposing a surface of a part to exhaust-gas, cleansing the surface exposed to the exhaust gas with a solvent, and measuring the electric conductivity of the solvent after the exposure.

The part is at least one of achromatic or transparent component. There can also be a step of quantifying the acidic matter, selectively at least one of NOx or SOx in the exhaust gas.

In some forms the exhaust gas is gas emitted from an internal combustion engine or a plant or factory facility. The gas can be directed from an exhaust gas inlet to an exhaust-gas outlet. This includes having a pass-through cavity between the inlet and outlet, and the diameter of the pass-through cavity being larger than that of the exhaust gas inlet and exhaust-gas outlet.

The larger the pH value, the higher the density of acidic matter selectively SOx or NOx in the exhaust gas. The larger the electric conductivity, the higher the density of electrolytes, selectively SOx or Nox in the exhaust gas.

DRAWINGS

The above-mentioned features and objects of the present disclosure will become more apparent with reference to the following description taken in conjunction with the accompanying drawings wherein like reference numerals denote like elements and in which.

Figure 4:
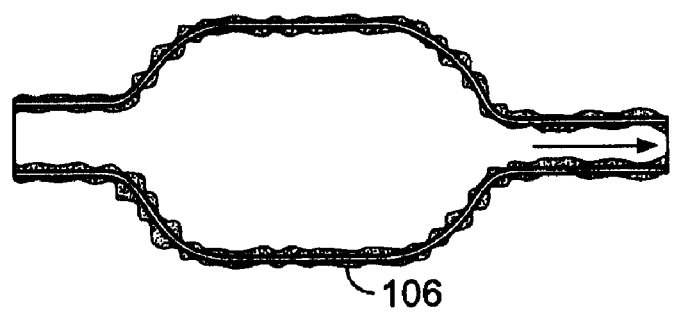

FIG. 4 explains one process in the method to measure exhaust-gas components in one embodiment of this disclosure.

Figure 5:
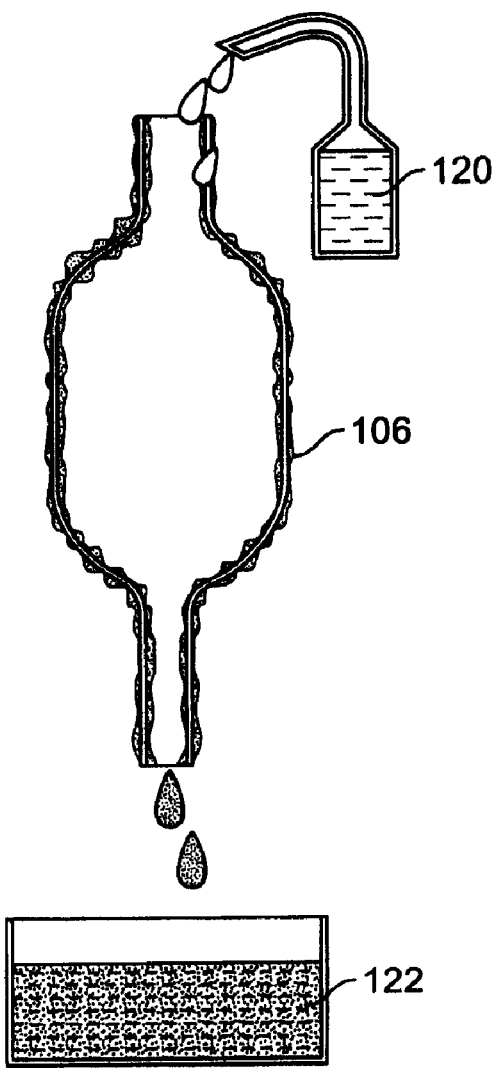

FIG. 5 explains one process in the method to measure exhaust-gas components in one embodiment of this disclosure.

FIG. 6 explains the part exposed to exhaust gas in the method to measure exhaust-gas components in experiment case 1 of this disclosure.

FIG. 7 explains the part exposed to exhaust gas in the method to measure exhaust-gas components in experiment case 2 of this disclosure.

FIG. 8 uses a venturi tube system to enable the measurement of P (pascal) in the tube.

FIGS. 9 and 10 show a tube with lids provided to the glass tube to inhibit or prevent collected exhaust gas components from spilling.

DETAILED DESCRIPTION

This disclosure concerns a method to measure exhaust-gas components containing various toxic chemical substances and particulate matter (PM), such as SOx and NOx.

The rising public interest in global environmental issues, there are increasing government activities to regulate the volume of pollutants emitted from internal combustion engines, such as automobiles and railroad locomotives. For instance, regulations are implemented on the emitted volume of particulate matter (PM), NOx, SOx, etc., put out by diesel-engine vehicles. These regulations are gradually being strengthened.

The term "PM" is a general one for particulate matter, the components of which are solid soot, SOF (Soluble Organic Fraction), mist of sulfuric acid (sulfate), nitrogen oxide, etc. The respective component ratios differ according to the engine type, driving condition, fuel type, etc. Solid soot is a lump of carbon, and it is generated in a large quantity when an engine is subjected to a high load. SOF is a particulate hydrocarbon of C15~C35 that can be extracted with dichloromethane, and it is generated in a large quantity when an engine is under a low load or started in a low-temperature environment. The mist of sulfuric acid is a mist form of the oxidized sulfur content (sulfur oxide) in the fuel that is resolved with water. Specifically, a PM forms with matter, such as SOF, mist of sulfuric acid, nitrogen oxide, etc., that surround the solid soot and adhere to it.

The size of a PM (particulate matter) is normally less than several deci-$\mu$m, but a particulate of less than 10 $\mu$m in diameter (which is said to be the cause of atmospheric pollution) is called suspended particulate matter (SPM), and especially a small one of less than 2.5 $\mu$m in diameter is called a PM 2.5. As explained above, a PM 2.5 is far smaller than an SPM and enters into the depths of a lung more often than a SPM. It is highly likely to cause an allergic disease such as asthma or bronchitis.

NOx is so-called nitrogen oxide, which is formed through the combination of nitrogen ($N_2$) and oxygen ($O_2$) in the atmosphere under a high temperature. For example, NO, $NO_2$ and $N_2O$ are collectively referred to as NOx. SOx is so-called a sulfur oxide, which is formed by the oxidized sulfur content in the fuel. Samples of SOx include $SO_2$, $SO_3$ and $SO_4^{2-}$.

Increased government activities in recent years have been designed to regulate the volume of pollutants in exhaust gas. Accordingly, there has emerged a demand for a method of measuring the components of exhaust gas more conveniently. "Health Effects of Diesel Exhaust," a special report by the HEI Diesel Working Group in the United States, Health Effects Institute, Author, translated by Tsuyoshi Kobayashi, issued by the Industrial Environment Control Association in December 1999.

The method used in this disclosure to measure exhaust-gas components includes:

A process to expose a part's surfaces to exhaust gas; a process to cleanse the surfaces exposed to the exhaust gas with a solvent; and a process to measure pH of the solvent obtained by the above cleansing process.

For example, the chief acidic matter in the exhaust gas put out by general internal-combustion engines of automobiles, diesel locomotives and railroad maintenance vehicles, etc. are NOx and SOx. Using the method of this disclosure to measure exhaust-gas components, it will be possible to quantify the acidic matter (NOx and SOx for example) in exhaust gas comprehensively and conveniently, by including a process to measure the pH of the said solvent obtained by cleansing the said surfaces exposed to the said exhaust gas.

The method to measure exhaust-gas components by this disclosure includes:

A process to expose a part's surfaces to exhaust gas; a process to cleanse the surfaces exposed to the exhaust gas with a solvent; and a process to measure the electric conductivity of the solvent obtained by the above cleansing process.

Using the method of this disclosure to measure exhaust-gas components, it is possible to quantify the electrolytes (NOx and SOx for example) contained in exhaust gas comprehensively and conveniently, particularly through the inclusion of a process to measure the electric conductivity of the above-mentioned solvent obtained in cleansing said surfaces exposed to the exhaust gas.

The surfaces of human and animal eyes are exposed to exhaust gas in the same way that the surfaces of a part are exposed to exhaust gas in the method to measure exhaust-gas components by this disclosure.

The process to expose the surfaces of a part to exhaust gas in the method of measuring exhaust-gas components by this disclosure is an imitation of the condition in which the surfaces of human and animal eyes are exposed to exhaust gas. Therefore, by using the method to measure exhaust-gas components with this disclosure, it is possible to reproduce the phenomena that are occurring on the surfaces of human and animal eyes when they are exposed to exhaust gas, and to analyze the acidic matter generated on the eye surfaces and the electrolytes attached to the surface of the eyes.

By using the method to measure exhaust-gas components with this disclosure, it is possible to measure components (acidic matter and/or electrolytes) in exhaust gas more conveniently than conventional measuring devices do.

The composition of exhaust gas tends to change when its pressure changes. However, by using the method to measure exhaust-gas components with this disclosure, it is possible to measure the exhaust-gas components without changing the pressure of the exhaust gas. Thus it is possible to measure the components of exhaust gas that has not changed its composition.

In the method to measure exhaust-gas components the part can be achromatic and transparent. With this composition it is possible to recognize more conveniently (with the naked eye) the condition of the matter attached to the surfaces by the exhaust gas.

Figure 1:
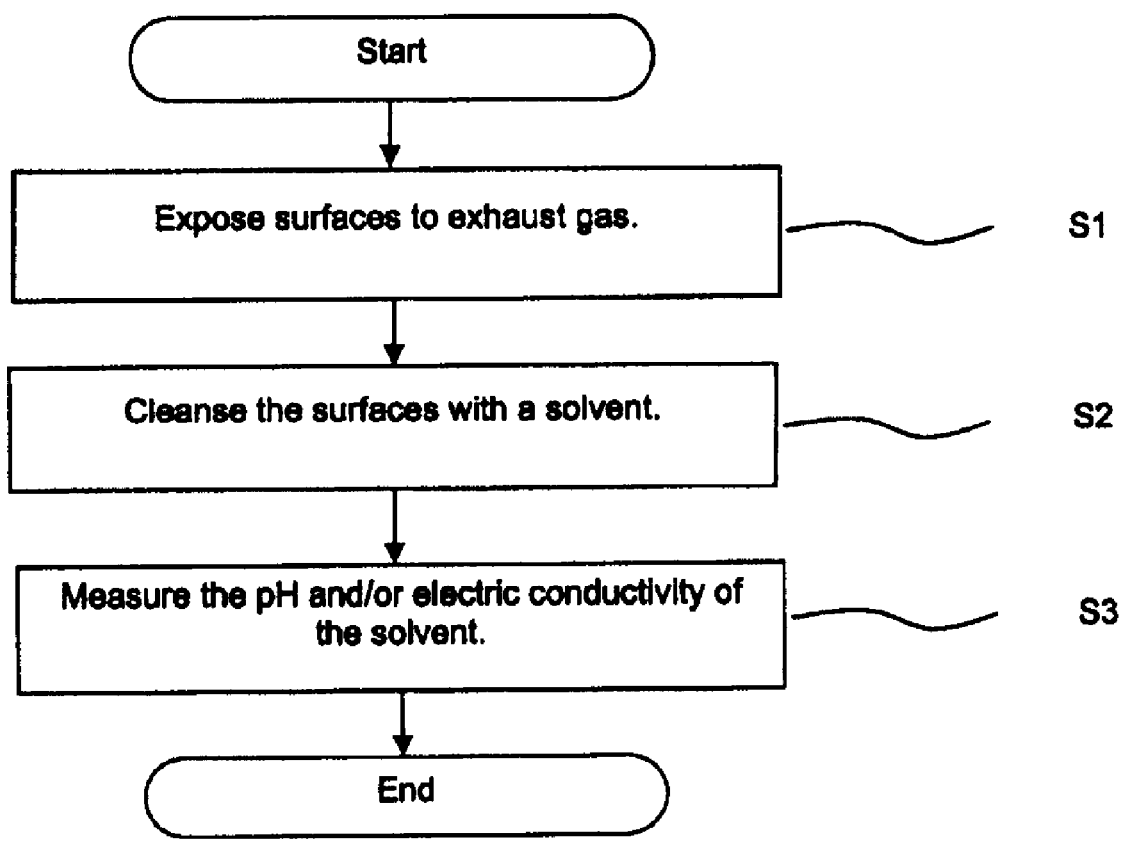
FIG. 1 shows a flowchart that explains each process of the method to measure exhaust-gas components in one embodiment of this disclosure.
Figure 2:
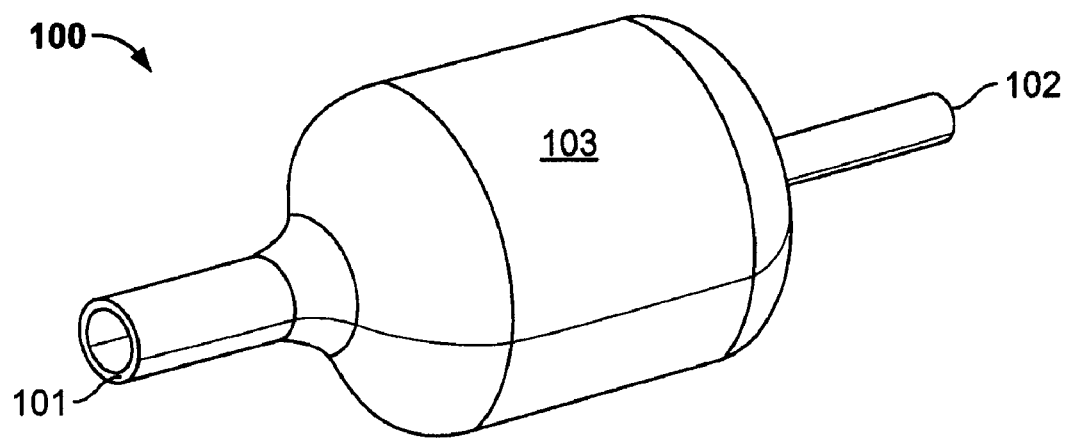
FIG. 2 shows a side view of a model of the part used in the method to measure exhaust-gas components in one embodiment of this disclosure.
Figure 3:
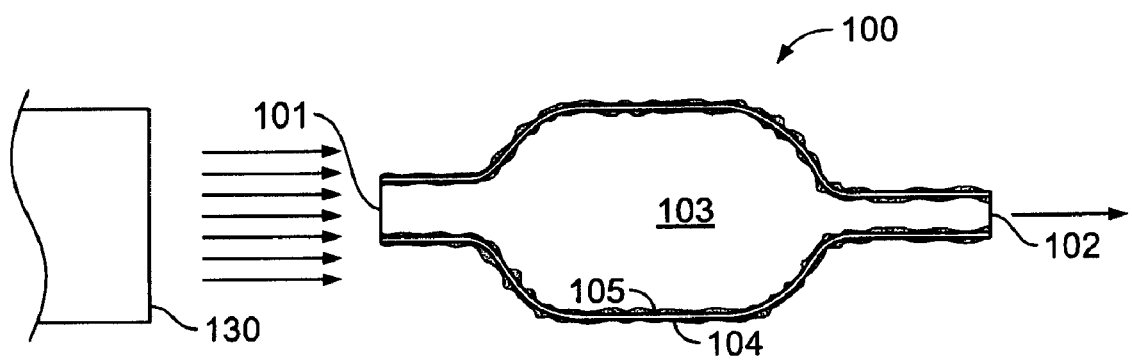
FIG. 3 shows one aspect of the method to measure exhaust-gas components in at least one embodiment of this disclosure.

The method to measure exhaust-gas components in the embodiment with reference to drawings is explained. FIG. 1 is a flowchart explaining each process of the method to measure exhaust-gas components in one format as a means to implement this disclosure. FIG. 2 is a side view of a model of the part used in the method to measure exhaust-gas components in one embodiment of this disclosure. FIGS. 3 to 5 respectively explain each process of the method to measure exhaust-gas components in one embodiment of this disclosure.

The method to measure exhaust-gas components in this embodiment includes the process to expose the surfaces 104 and 105 of a part 100 to exhaust gas. Step S1 of FIG. 1, FIG. 3 and FIG. 4. The process is to cleanse the surfaces 104 and 105 exposed to the said exhaust gas with the solvent 120. Step S2 in FIG. 1 and FIG. 5. The process measuring the pH and/or electric conductivity of the solvent 120 in the above-mentioned cleansing process. Step S3 in FIG. 1.

As indicated in FIG. 3, the part 100 is placed near the exhaust-gas outlet 130, and the surfaces 104 and 105 of this part 100 are exposed to the exhaust gas. Step S1 in FIG. 1. Specifically, the exhaust gas inlet 101 of the part 100 is placed near the exhaust-gas outlet 130. Thus at least a part of the exhaust gas that is put out flows inside the part 100 from the exhaust gas inlet 101. After passing through the pass-through cavity 103, the exhaust gas is put out from the exhaust-gas outlet 102.

In this embodiment, the exhaust gas refers to the gas emitted from an internal combustion engine or a plant or factory facility. An internal combustion engine, without any special limitation, is a gasoline engine, diesel engine or jet engine. There are increasing government activities in recent years to regulate the quantities of NOx and SOx emitted from diesel engines among them. This embodiment of the method to measure exhaust-gas components can be used to quantify the NOx and SOx emitted from a diesel engine. Examples of equipment that contain an internal combustion engine, with any particular limitations, are an automobile, a generator, a ship and an electric train. For example, there is a passenger train, a freight train or a maintenance train.

The part 100 is placed in such a way that a part of its surfaces are exposed to the exhaust gas. The shape of the part 100 is not limited to anything specific, as long as it has adequate surface areas on which to accumulate a sufficient quantity of attachments when exposed to the exhaust gas for the measurement of pH and/or electric conductivity. The material for the part 100 is not limited to anything specific, as long as it is durable against the solvent used in the cleansing process that is described later. For example, part 100 is achromatic and transparent. Such a part makes it easier to visually recognize the attachments to the surfaces after they are exposed to the exhaust gas.

This part 100 may have a pass-through cavity 103. With this structure, the part 100 contacts the exhaust gas on its inner surface 105 and the outer surface 104, so that its surface areas that contact the exhaust gas are increased. Specifically, this part 100 includes an exhaust gas inlet 101, an exhaust-gas outlet 102 and a pass-through cavity 103. The exhaust passes through from the exhaust gas inlet 101 to the exhaust-gas outlet 102. The diameter of the pass-through cavity 103 may be larger than that of the exhaust gas inlet 101 and that of the exhaust-gas outlet 102. When this part 100 with this structure is placed near the equipment's exhaust-gas outlet 130, the components of the exhaust gas will more easily attach to the surfaces 104 and 105. It is possible to analyze the exhaust-gas components with more certainty.

As shown in FIG. 4, the above process collects attachments 106 to surfaces 104 and 105 of the part 100. These attachments 106 were formed by the pollutants in the exhaust gas that contacted the surfaces 104 and 105. The main component of these attachments 106 is PM. The PM contains solid soot, SOF, SOx, such as mist of sulfuric acid (sulfate), and nitrogen oxide (NOx). The main components of acidic matter and electrolytes in the attachment 106 are usually SOx and NOx.

FIG. 5 shows surfaces 104 and 105 that have been exposed to the exhaust gas are cleansed with solvent 120. Step S2 in FIG. 1. The solvent used in the cleansing 122 is collected.

The solvent 120 is not particularly limited to anything, as long as it can dissolve attachments 106. For example, there is methanol, ethanol, n-propanol, iso-propanol, acetone, methyl ethyl ketone, aceto-nitryl, dimethyl sulfoxide, or any of the above solvents mixed with water.

The pH and/or electric conductivity of solvent 122 obtained in the above cleansing process are measured Step S3 in FIG. 1. Any pH meter that is publicly available to measure the pH, and any electric conductivity meter that is publicly available to measure the electric conductivity.

By using this embodiment of the method to measure exhaust-gas components, which includes a process to measure the pH of solvent 122 obtained when cleansing surfaces 104 and 105 that were exposed to exhaust gas, we can easily measure the density of the acidic matter (for example, NOx and SOx) in the exhaust gas. Also, by this embodiment of the method to measure exhaust-gas components, which includes a process to measure the electric conductivity of solvent 122 obtained when cleansing surfaces 104 and 105 that were exposed to exhaust gas, we can comprehensively quantify the electrolytes (NOx and SOx for example) contained in the exhaust gas.

By using the parts 100 of the same size and shape and the same quantities of solvent 120 for cleansing different exhaust gases, by applying the method of this embodiment, and by comparing the measured pH (and/or electric conductivity) values, we can compare the densities of the acidic matter (and/or electrolytes) in the exhaust gases. In this case, the larger the pH value, the higher the density of acidic matter (SOx or NOx, for example) in the exhaust gas, and that the larger the electric conductivity, the higher the density of electrolytes (SOx or NOx, for example) in the exhaust gas.

By using this embodiment of the method to measure exhaust-gas components, including the process to measure the pH and/or electric conductivity of the solvent obtained when cleansing the surfaces exposed to exhaust gas, we can comprehensively and conveniently quantify the acidic matter and electrolytes (SOx or NOx, for example) in the exhaust gas.

By using this embodiment of the method to measure exhaust-gas components, we can reproduce the phenomenon that occurs on the surfaces of human or animal eyes when they are exposed to exhaust gas, and analyze the acidic matter and electrolytes attached to the eye surfaces.

Through such embodiment of the method to measure exhaust-gas components, we can measure the exhaust-gas components (acidic matter and/or electrolytes) more conveniently than using the conventional measurement devices.

By using this embodiment of the method to measure exhaust-gas components, no change is made to the pressure of the exhaust gas. Thus it can measure the exhaust-gas components without changing the composition of the exhaust gas.

This disclosure more specifically by citing examples of embodiments. However, the following descriptions indicate only some general embodiments of this disclosure without particular reasons. Thus these descriptions shall not limit this disclosure.

Experiment Case 1

An achromatic and transparent glass part with a shape as shown in FIG. 2 was placed near the exhaust-gas outlet of a 4-ton truck and exposed to the exhaust gas for 3 hours (refer to the FIGS. 3 and 4). FIG. 6 shows a figure of the part after 3 hours' exposure to the exhaust gas. The surfaces (outer and interior surfaces) of this part exposed to the exhaust gas are cleansed with a solvent (10% ethanol eluent) (refer to FIG. 5). Then measuring the pH and electric conductivity of the solvent collected after cleansing. Table 1 shows the results.

Experiment Case 2

An achromatic and transparent glass part with a shape as shown in FIG. 2 was placed near the exhaust-gas outlet of a rail-maintenance vehicle and exposed to the exhaust gas for 2 hours (refer to the FIGS. 3 and 4). FIG. 7 shows a photo of the part after 2 hours' exposure to the exhaust gas. Next the surfaces (outer and interior surfaces) of this part exposed to the exhaust gas were cleansed with a solvent (20% ethanol eluent). Refer to FIG. 5. We then measured the pH and electric conductivity of the solvent collected after cleansing. Table 1 shows the results.

TABLE 1

|  | pH | Electric Conductivity μS/cm |
|---|---|---|
| Experiment Case 1 | 4.20 | 0.803 |
| Experiment Case 2 | 4.05 | 1.197 |
| Comparison Case 1 | 8.40 | 0.083 |
| Comparison Case 2 | 6.91 | 0.026 |

In the above Table 1, comparison case 1 shows the measured pH and electric conductivity of 10% ethanol eluent, while comparison case 2 shows the measured pH and electric conductivity of 20% ethanol eluent. Table 1 shows that in both experiment cases 1 and 2 the pH of the solvent collected after cleansing was lower than that before cleansing. Through such result it is confirmed that the matter that attached to the part when it is exposed to exhaust gas in experiment cases 1 and 2 contained acidic matter. Moreover, the electric conductivity of the solvent collected after cleansing in both experiment cases 1 and 2 was higher than that before cleansing. The result is confirmed that the matter that is attached to the part when it is exposed to exhaust gas in experiment cases 1 and 2 contains electrolytes.

Judging from the above results, the attachments to the part after it was exposed to exhaust gas in experiment cases 1 and 2 contain acidic and electrolytic matter. Such matter is estimated to be NOx and SOx. Therefore, it is possible to detect the densities of NOx and SOx in the exhaust gas by experiment cases 1 and 2.

FIG. 8 uses a venturi tube system 200 to enable the measurement of P (pascal) in the tube. This type of glass tube is used specifically to measure exhaust gas components from engines with different exhaust-gas amount. the gas would enter through inlet 202 as indicated by arrow 204. The gas outlet is 206 as indicted by arrow 208. Through the pressure measuring tube 210 in the larger diameter portion 212 and the tube 214 in the narrower portion 216, it is possible by measuring the difference in pressures to obtain the requisite measurements for the disclosure.

The venturi effect is a metering or measuring manner so that pressure in the larger diameter part of the tube is higher than at the narrower portion. The Venturi effect causes the fluid or air flow through the narrower tube to speed up at the same as reducing pressure and producing a partial vacuum A fluid passing through smoothly varying constrictions is subject to changes in velocity and pressure in order to satisfy the conservation of mass-flux (flow rate). The pressure gradient reduces the pressure in the constriction, in reaction to the acceleration. This Venturi effect is a choked flow, in which a constriction in a pipe or channel limits the total flow rate through the channel, because the pressure cannot drop below zero in the constriction. The pascal is measured, and thereby the level of pressure is obtained thereby to obtain the measurement data of the disclosure.

In FIGS. 9 and 10 there is a container 218 with a large lid 220 and a smaller lid 222 provided to the glass tube to inhibit or prevent collected exhaust gas components from spilling. These lids 220 and 222 fit the respective openings 224 and 226. The gas would otherwise flow as indicated by arrows 228 and 230. The accuracy of measurement of gases in terms of the disclosure can be enhanced by this system.

While the apparatus and method are described in terms of what are presently considered to be the most practical and preferred embodiments, it is understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

The invention claimed is:

1. A method of measuring exhaust-gas components comprises exposing a surface of a part to exhaust gas from an internal combustion engine or a plant or factory facility, wherein particulate matter of the exhaust gas collects on the surface of the part, cleansing the surface exposed to the exhaust gas with a solvent thereby removing the particulate matter from the surface, and measuring the pH of the solvent having particulate matter obtained from the cleansing process in order to determine the density of electrolytes in the exhaust gas.

2. A method of measuring exhaust-gas components comprises exposing a surface of a part to exhaust gas from an internal combustion engine or a plant or factory facility, wherein particulate matter of the exhaust gas collects on the surface of the part, cleansing the surface exposed to the exhaust gas with a solvent thereby removing the particulate matter from the surface, and measuring the electric conductivity of the solvent having particulate matter obtained from the cleaning process, in order to determine the density of electrolytes in the exhaust gas.

3. A method of claim 1 or 2 wherein the part that is at least one of achromatic or transparent component.

4. A method of claim 1 or 2 including quantifying the acidic matter, selectively at least one of NOx or SOx in the exhaust gas.

5. A method of claim 1 or 2 wherein the gas is directed from an exhaust gas inlet to an exhaust-gas outlet and including having a pass-through cavity between the inlet and outlet, and the diameter of the pass-through cavity being larger than that of the exhaust gas inlet and exhaust-gas outlet.

6. A method of claim 1 or 2 wherein the solvent contains selectively at least one of methanol, ethanol, n-propanol, iso-propanol, acetone, methyl ethyl ketone, aceto-nitryl, dimethyl sulfoxide, and wherein the solvent selectively includes water.

7. A method of claim 1 wherein the larger the pH value, the higher the density of acidic matter selectively SOx or NOx, in the exhaust gas.

8. A method of claim 2 wherein the larger the electric conductivity, the higher the density of electrolytes, selectively SOx or NOx in the exhaust gas.

9. A method of claim 1 or 2 wherein the exhaust gas is gas emitted from an internal combustion engine or a plant or factory and including passing the gas into a measuring container.

10. A method of claim 1 or 2 wherein the exhaust gas is gas emitted from an internal combustion engine or a plant or factory and including passing the gas into a measuring container and into a venturi restriction in the container.

11. A method of claim 1 or 2 wherein the exhaust gas is gas emitted from an internal combustion engine or a plant or factory and including sealing the container with the collected gases prior to measurement.

* * * * *